(12) United States Patent
Brock-Fisher

(10) Patent No.: US 9,950,342 B2
(45) Date of Patent: Apr. 24, 2018

(54) CAPACITIVE MICRO-MACHINED ULTRASOUND TRANSDUCER DEVICE WITH CHARGING VOLTAGE SOURCE

(71) Applicant: KONINKLIJKE PHILIPS N.V., Eindhoven (NL)

(72) Inventor: George Anthony Brock-Fisher, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 421 days.

(21) Appl. No.: 14/382,560

(22) PCT Filed: Mar. 1, 2013

(86) PCT No.: PCT/IB2013/051631
§ 371 (c)(1),
(2) Date: Sep. 3, 2014

(87) PCT Pub. No.: WO2013/136212
PCT Pub. Date: Sep. 19, 2013

(65) Prior Publication Data
US 2015/0016227 A1    Jan. 15, 2015

Related U.S. Application Data

(60) Provisional application No. 61/610,130, filed on Mar. 13, 2012.

(51) Int. Cl.
*G01V 1/137* (2006.01)
*B06B 1/02* (2006.01)
*G01N 29/24* (2006.01)

(52) U.S. Cl.
CPC ....... *B06B 1/0292* (2013.01); *G01N 29/2406* (2013.01)

(58) Field of Classification Search
USPC ........................................................ 367/181
See application file for complete search history.

(56) References Cited

U.S. PATENT DOCUMENTS 6,328,696 B1   12/2001  Fraser
7,995,423 B2    8/2011  Hideo
(Continued)

FOREIGN PATENT DOCUMENTS

EP    1781067 A1    5/2007
JP    2008005885 A  1/2008
JP    2009272824 A  11/2009

OTHER PUBLICATIONS

Wong, Serena H., et al. "Capacitive micromachined ultrasonic transducers for therapeutic ultrasound applications." IEEE transactions on Biomedical Engineering 57.1 (2010): 114-123.*
(Continued)

*Primary Examiner* — Isam A Alsomiri
*Assistant Examiner* — Jonathan D Armstrong

(57) ABSTRACT

The present invention relates to a capacitive micro-machined ultrasound transducer (CMUT) device (1) for transmitting and/or receiving ultrasound waves, comprising at least one CMUT cell (10). The CMUT cell (10) comprises a substrate (13) comprising a first electrode (22), a membrane (15) comprising a second electrode (20), at least one dielectric layer (21, 23) between the first electrode (22) and the second electrode (20), and a cavity (18) formed between the substrate (13) and the membrane (15). The CMUT device (1) further comprises an operating bias voltage source (25) for supplying an operating bias voltage ($V_B$) of a first polarity between the first and second electrode (20, 22) during transmitting and/or receiving ultrasound waves, and a charging voltage source (30) for supplying an additional charging voltage ($V_C$) between the first and second electrode (20, 22), the second polarity being the reverse (Continued)

polarity of the first polarity. The present invention further relates to a method of operating such a CMUT device.

15 Claims, 5 Drawing Sheets

(56) References Cited

U.S. PATENT DOCUMENTS

| | | |
|---|---|---|
| 2007/0140515 A1 | 6/2007 | Oliver |
| 2007/0161896 A1 | 7/2007 | Hideo |
| 2009/0299192 A1* | 12/2009 | Asafusa ............... B06B 1/0292 600/459 |
| 2009/0301199 A1* | 12/2009 | Azuma .................. A61B 8/08 73/603 |
| 2010/0168583 A1 | 7/2010 | Dausch et al. |
| 2010/0237807 A1 | 9/2010 | Lemmerhirt |
| 2010/0254222 A1 | 10/2010 | Huang |
| 2016/0310992 A1* | 10/2016 | Van Rens ............. B06B 1/0292 |

OTHER PUBLICATIONS

WO2013136212. International Search Report and Written Opinion. International Publication dated Sep. 19, 2013 (Sep. 19, 2013).*
"Charge Storage in Double Layers of Silicon Dioxide and Silicon Nitride" Houman Amjadi, Telecommunication and Electroacoustics, Techincial Paper University of Darmstadt, Germany, 1996 IEEE, p. 22-27.
"Analysis of Charge Effects in High Frequency CMUTS" Midtbo et al, 2008 IEEE International Ultrasonics Symposium Proceedings, p. 379-382.

* cited by examiner

CAPACITIVE MICRO-MACHINED ULTRASOUND TRANSDUCER DEVICE WITH CHARGING VOLTAGE SOURCE

This application is the U.S. National Phase application under 35 U.S.C. § 371 of International Application No. PCT/IB2013/051631, filed on Mar. 1, 2013, which claims the benefit of U.S. Provisional Application No. 61/610,130 filed on Mar. 13, 2012. These applications are hereby incorporated by reference herein.

FIELD OF THE INVENTION

The present invention relates to a capacitive micro-machined ultrasound transducer device (CMUT) device for transmitting and/or receiving ultrasound and to a method of operating the same. The present invention can for example be used in a medical ultrasound system (e.g. diagnostic or therapeutic medical ultrasound system), in particular with ultrasound imaging functionality.

BACKGROUND OF THE INVENTION

The heart of any ultrasound (imaging) system is the transducer device with its transducer elements or transducer cells which convert electrical energy in acoustic energy and back. Traditionally, these transducer elements or transducer cells are made from piezoelectric crystals arranged in linear (1-D) transducer arrays, and operating at frequencies up to 10 MHz. However, the trend towards matrix (2-D) transducer arrays and the drive towards miniaturization to integrate ultrasound (imaging) functionality into catheters and guide wires has resulted in the development of so-called capacitive micro-machined ultrasound transducer (CMUT) devices.

A CMUT cell comprises a membrane (or diaphragm), a cavity underneath the membrane, and electrodes forming a capacitor. For receiving ultrasound waves, ultrasound waves cause the membrane to move or vibrate and the variation and capacitance between the electrodes can be detected. Thereby, the ultrasound waves are transformed into a corresponding electrical signal. Conversely, an electrical signal applied to the electrodes causes the membrane to move or vibrate and thereby transmitting ultrasound waves. In other words, when an electrical signal or voltage is applied to the electrodes forming the capacitor, the electric signal or voltage causes the membrane to deflect, thereby creating ultrasound pressure waves. Typically, a CMUT cell is manufactured using microelectronic semiconductor fabrication techniques. The CMUT device offers advantages in terms of frequency coverage and ease of fabrication over contemporary piezoelectric transducer devices. However, CMUT devices currently may still have a disadvantage in terms of the efficiency and acoustic pressure output relative to existing piezoelectric transducer devices.

In an attempt to increase acoustic pressure output, an operating bias voltage applied or supplied between the electrodes can be increased. However, there are limits to the operating bias voltage that can be applied due to dielectric breakdown and charged tunneling effects. There may also be limits to the operating bias voltage due to driving circuitry, for example in the form of an application specific integrated circuit (ASIC). A problem with applying an increased or excessive operating bias voltage can be that the membrane collapses to the substrate and thereby the electrodes may electrically contact each other. In order to separate the electrodes and thereby prevent electrical contact between the electrodes, the CMUT cell can comprise a dielectric layer or dielectric layers between the electrodes. In particular, a first dielectric layer on or as part of the substrate and a second dielectric layer on or as part of the membrane can be used.

It is a currently recognized limitation of CMUT device that if excessive operating bias voltages are applied to the device, the dielectric layers used to separate the electrodes can become more or less permanently charged. This charging effect has been recognized and deemed a problem or "reliability issue" and an undesirable side effect of the construction of the device. In particular, the permanent charge of the dielectric layers reduces the efficiency of the device as an acoustic transducer device. If the output pressure of a CMUT device is measured at a low unipolar bias voltage and if then this bias voltage is increased to a level sufficient to charge the dielectric layers, the CMUT device will show a lower output pressure when driven by the original low bias voltage.

U.S. 20100237807 A1 discloses a system and method for biasing a capacitive ultrasonic transducer (CMUT) device with a circuit that includes a CMUT that includes a first plate and a second plate that form a membrane structure; a circuit voltage source at a complementary metal-oxide-semiconductor (CMOS) compatible voltage; a bias voltage source that applies a bias voltage greater than a CMOS compatible voltage and is applied to the first plate; and readout electronics with an input connected on the second plate side of the circuit. In an embodiment, the bias voltage alternates polarity according to events related to receiving or transmission of a signal. For example, a bias source may be used that alternates polarity periodically during the ultrasound imaging procedure, as opposed to a DC bias source. This may be used to resolve the charging problems that arise while holding CMUTs at constant DC bias.

SUMMARY OF THE INVENTION

It is an object of the present invention to provide an improved CMUT device, in particular with increased output pressure and/or receive sensitivity, and a method of manufacturing the same.

In a first aspect of the present invention a capacitive micro-machined ultrasound transducer (CMUT) device for transmitting and/or receiving ultrasound waves is presented, comprising at least one CMUT cell. The CMUT cell comprises a substrate comprising a first electrode, a membrane comprising a second electrode, at least one dielectric layer between the first electrode and the second electrode, and a cavity formed between the substrate and the membrane. The CMUT device further comprises an operating bias voltage source for supplying an operating bias voltage of a first polarity between the first and second electrode during transmitting and/or receiving ultrasound waves, and a charging voltage source for supplying an additional charging voltage between the first and second electrode, the second polarity being the reverse polarity of the first polarity.

In a further aspect of the present invention, a method of operating a capacitive micro-machined ultrasound transducer (CMUT) device comprising at least one CMUT cell comprising a substrate comprising a first electrode, a membrane comprising a second electrode, at least one dielectric layer between the first electrode and the second electrode, and a cavity formed between the substrate and the membrane is presented. The method comprises the steps of supplying an operating bias voltage of a first polarity between the first and second electrode during transmitting and/or receiving ultrasound waves, and supplying an additional charging voltage between the first and second electrode, the second polarity being the reverse polarity of the first polarity.

The basic idea of the invention is to actually use the effect of trapped charges in the dielectric layer(s) (also called charging effect) to increase output pressure and/or receive sensitivity of the CMUT device. This is different from the prior art where it has always been tried to resolve or reduce the effects of charges in the dielectric layer(s). Using the charging effect is achieved by supplying or applying an additional or intentional charging voltage, in particular a DC voltage, between the electrodes having the reverse (or opposite) polarity of the polarity of the usual operating bias voltage. In other words, the charging voltage is applied to intentionally charge the dielectric layer(s) of the CMUT cell. For example, the membrane of the CMUT cell can comprise a first dielectric layer and the substrate can comprise a second dielectric layer.

The term operating bias voltage describes a bias voltage supplied during an operation phase of the CMUT device, i.e. during transmitting and/or receiving of ultrasound waves. The additional charging voltage is in particular not supplied during an operation phase, i.e. not during transmitting and/or receiving of ultrasound waves. For example, if first an additional charging voltage is supplied or applied and then the operating bias voltage during an operation phase has the reverse polarity to the charging voltage, the output pressure or receive sensitivity of the device can be significantly increased (e.g. by a factor of two or more). Therefore, the effect of charges in the dielectric layer(s) (charging effect) is used to increase output pressure or receive sensitivity.

In particular, by applying a sufficient charging voltage, a semi-permanent voltage is impressed on the electrodes of the CMUT device. This semi-permanent voltage is caused by charge carriers trapped in the dielectric layer(s) so they do not quickly bleed off. This voltage essentially adds to any applied operating bias voltage, thus allowing higher effective forces on the membrane for a given externally applied voltage.

Preferred embodiments of the invention are defined in the dependent claims. It shall be understood that the claimed method has similar and/or identical preferred embodiments as the claimed device and as defined in the dependent claims.

In a first embodiment, the charging voltage is supplied during manufacturing of the CMUT device such that it remains in the at least one dielectric layer substantially permanently. With substantially permanently it is meant that the charge remains throughout the useful life of the device. In this way a substantially permanent charge is applied to the dielectric layers(s) during manufacturing and remains throughout the useful life of the device. This is a particularly easy way of providing the charging voltage or charge, without much modification of a conventional CMUT device. Thus, the costs of the device are not substantially increased. In one example, the charging voltage source can be an external voltage source which can be disconnected from the CMUT device after charging. In an alternative example, the charging voltage source can be an internal voltage source of the device which may later on (e.g. during the useful life of the device) be used to reapply the charging voltage.

In a second embodiment, the CMUT device further comprises a control unit for controlling the operating bias voltage source and/or the charging voltage source to control the charge in the at least one dielectric layer. This may in particular be necessary if it is found that the charge cannot be permanently maintained in the dielectric layer(s). In this way, the additional charging voltage can be supplied when actually using the device, as opposed to manufacturing the device. This provides for a greater flexibility. For example, the control unit can be implemented in a driving circuitry, such as an ASIC, of the CMUT device. In this way, the costs of the device are not substantially increased.

In a further embodiment or variant, the control unit is adapted to control the operating bias voltage source to supply the operating bias voltage for a long enough time period to provide significant accumulation of charge in the at least one dielectric layer. In this way it is ensured that a significant charging effect is present. In an alternative or cumulative embodiment or variant, the control unit is adapted to control the charging voltage source to supply the charging voltage for a long enough time period to charge the at least one dielectric layer to increase output pressure and/or receive sensitivity of the CMUT cell. In this way the charging effect is optimally used.

In another embodiment or variant, the control unit is adapted to control the operating bias voltage source to supply the operating bias voltage for a first time period during transmitting and/or receiving ultrasound waves. Alternatively or cumulatively, the control unit is adapted to control the charging voltage source to supply the charging voltage for a second time period during no transmitting and/or receiving of ultrasound waves. In this way it is ensured that the operating bias voltage and the charging voltage are not applied during the same time. In particular, it is ensured that the operating bias voltage is supplied during an operation phase of the device, and that the charging voltage is not supplied during such an operation phase. In one example, the second time period is before the first time period. In another example, the second time period is after the first time period. In yet another example, the second time period is in between two first time periods.

In another embodiment or variant, the control unit is adapted to control the charging voltage source to supply the charging voltage periodically. In particular, the charging voltage can be supplied before each scan line or before each frame. In this way, the device is intentionally charged in such a way as to increase output pressure and/or receive sensitivity during subsequent operation. In this way it is ensured that the output pressure and/or receive sensitivity is increased permanently. This increases performance and/or reliability of the device.

In yet another embodiment or variant, the control unit is adapted to control the operating bias voltage source to supply the operating bias voltage at a first voltage level, and to control the charging voltage source to supply the charging voltage at a second voltage level different from the first voltage level. Thus, the voltage level of the charging voltage does not need to be the same as the voltage level of the operating bias voltage. This increases flexibility of the device. In one example, the second voltage level can be smaller than the first voltage level. In an alternative example, the second voltage level can be greater than the first voltage level.

In another embodiment, the CMUT device further comprises a monitoring unit for monitoring the charge in the at least one dielectric layer. In this way it can be monitored or checked if the charge in the dielectric layer(s) can still increase the output pressure and/or receive sensitivity of the device. This improves functionality of the device. For example, the monitoring unit can be implemented in a driving circuitry, such as an ASIC, of the CMUT device. In this way, the costs of the device are not substantially increased.

In a variant of this embodiment, the monitoring unit is adapted to monitor a shift in a capacitance-versus-voltage curve of the CMUT device. This is one efficient way of monitoring the charge in the dielectric layer(s). In an alternative or cumulative variant of this embodiment, the monitoring unit is adapted to monitor the output pressure and/or receive sensitivity while varying the charging voltage. In particular, a charging voltage can be determined that results in minimum acoustic pressure and/or sensitivity. This is another efficient way of monitoring the charge in the dielectric layer(s). In this way or these ways the monitoring can be implemented in a particularly easy manner.

In yet another variant of this embodiment, the monitoring unit is adapted to detect when the charge in the at least one dielectric layer is insufficient. In this way it can be monitored or checked if the charge in the dielectric layer(s) has become insufficient so that an action needs to be taken. This improves reliability of the device. For example, the monitoring unit can be adapted to compare the currently monitored charge with a predefined value. In one example, the current shift in the capacitance-versus-voltage curve can be compared with a predefined value. In another embodiment, the current output pressure and/or receive sensitivity can be compared with a predefined value.

In a further embodiment or variant, the control unit is adapted to control the charging voltage source to reapply the charging voltage when the monitoring unit detects that the charge in the at least one dielectric layer is insufficient. In this way the charge in the dielectric layer(s) can be refreshed over the useful life of the CMUT device. This enables to sustain improved output pressure and/or receive sensitivity. In this way the performance and/or reliability of the device are increased. For example, the CMUT device can be in its normal operation until a time, when the output pressure and/or receive sensitivity has decreased and the CMUT device needs to be charged again with the charging voltage to achieve the desired output pressure and/or receive sensitivity.

In another embodiment, the control unit and the monitoring unit are implemented in the same device. In particular, the control unit and the monitoring unit can be implemented in a driving circuitry, such as an ASIC, of the CMUT device. In this way, the costs of the device are not substantially increased.

In yet another embodiment, the CMUT device further comprises an alternating current source for supplying an alternating current between the first and second electrode for transmitting ultrasound waves. In this way, a conventional CMUT device is provided which transmits ultrasound waves (or pulses) and then receives the echoes of the transmitted ultrasound waves (or pulses). For example, the alternating current source can be controlled by a driving circuitry, such as an ASIC, of the device in a conventional manner.

In another embodiment, the CMUT device is a high-intensity focused ultrasound (HIFU) transducer device. In this way the charging effect can be used in an optimal way, because a high output pressure is required in an HIFU transducer device. A HIFU transducer device can for example be used in a medical system to heat and destroy pathogenic tissue rapidly through ablation.

In a further embodiment, the operating bias voltage source and the charging voltage source are implemented in one single voltage source. This reduces costs of the device. In an alternative embodiment, the bias voltage source and the charging voltage source are implemented as separate voltage sources. This increases flexibility of the device. For example, two different voltage levels can be implemented in this way.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
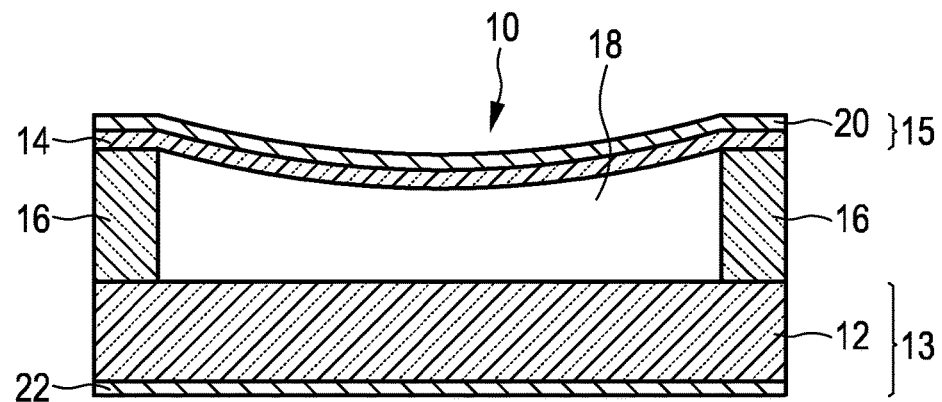
FIG. 1 shows a schematic cross-sectional view of a typical CMUT cell.

FIG. 1 shows a schematic cross-sectional view of a typical CMUT cell 10. The CMUT transducer cell 10 is normally fabricated along with a plurality of similar adjacent cells on a substrate 13. The substrate 13 comprises a substrate base layer 12. A diaphragm or membrane 15 is supported above the substrate by an insulating support 16. In this way a cavity 18 is formed between the membrane 15 and the substrate 13. The membrane 15 comprises a membrane base layer 14. The cavity 18 between the membrane and the substrate may be air or gas-filled or wholly or partially evacuated. A conductive film or layer forms a first electrode 22 in the substrate 13, and a similar film or layer forms a second electrode 20 in the membrane 15. These two electrodes 20, 22, separated by the cavity 18, form a capacitance or capacitor. When ultrasound waves in form of an acoustic signal cause the membrane 15 to vibrate the variation in the capacitance can be detected, thereby transducing or transforming the ultrasound waves into a corresponding electrical signal. Conversely, an alternating current (AC) or AC signal applied to the electrodes 20, 22 will modulate the capacitance, causing the membrane to move and thereby transmit ultrasound waves as an acoustic signal. In other words, for receiving ultrasound waves, ultrasound waves cause the membrane 15 to move or vibrate and the variation and capacitance between the electrodes 20, 22 can be detected. Thereby, the ultrasound waves are transformed into a corresponding electrical signal. Conversely, an electrical signal applied to the electrodes 20, 22 causes the membrane to move or vibrate and thereby transmitting ultrasound waves.

Figure 2:
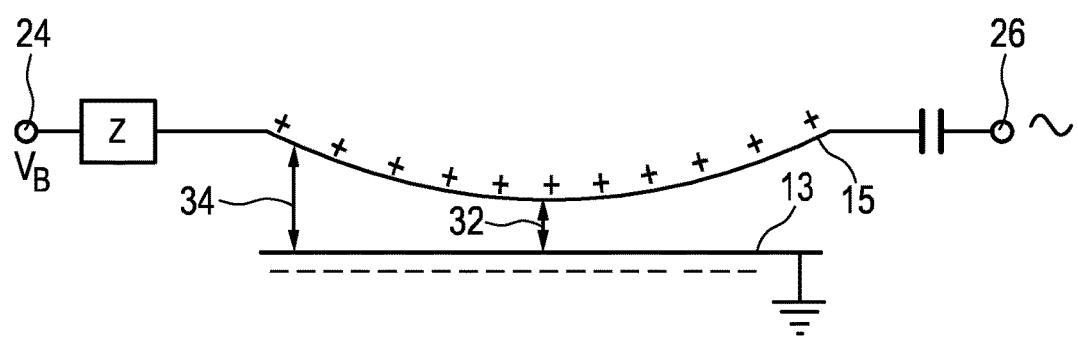
FIG. 2 shows a schematic illustration of the electrical properties of a typical CMUT cell.

The CMUT is inherently a quadratic device so that the acoustic signal is normally the harmonic of the applied signal, that is, the acoustic signal will be at twice the frequency of the applied electrical signal frequency. To prevent this quadratic behavior a bias voltage is typically applied to the two electrodes 20, 22 which causes the membrane 15 to be attracted to the substrate 13 by the resulting coulombic force. FIG. 2 shows a schematic illustration of the electrical properties of a typical CMUT cell. In FIG. 2 a CMUT cell is schematically shown where a DC bias voltage $V_B$ is applied to a bias terminal 24 and is coupled to the membrane electrode 20 by a path which poses a high impedance Z to AC signals, such as an inductive impedance. AC signals are capacitively coupled to and from the membrane electrode 20 from an AC signal terminal 26. The positive charge on the membrane 15 causes the membrane to distend as it is attracted to the negative charge on the substrate 13. It has been found that the CMUT cell is most sensitive when the membrane is distended so that the two oppositely charged plates of the capacitive device are as close together as possible. A close proximity of the two electrodes or plates will cause a greater coupling between acoustic and electrical signal energy. Thus it is desirable to increase the bias voltage $V_B$ until the dielectric spacing 32 between the membrane 15 and substrate 13 is as small as can be maintained under operating signal conditions. If the applied bias voltage is too great, however, the membrane 15 can contact the substrate 13, short-circuiting the device as the two electrodes or plates of the device are stuck together by VanderWals forces. This sticking can occur when the CMUT cell is overdriven, and can vary from one device to another with the same bias voltage $V_B$ due to manufacturing tolerance variations.

Permanent sticking can be reduced be providing an electrical isolation layer or dielectric layer between the electrodes 20, 22 or by embedding the electrodes 20, 22 therein. For example, a so-called ONO dielectric layer (made of layers of silicone oxide-silicone nitride-silicon oxide) can be used, as for example disclosed in WO 2010032156 A2, which is incorporated in its entirety by reference herein.

Figure 3:
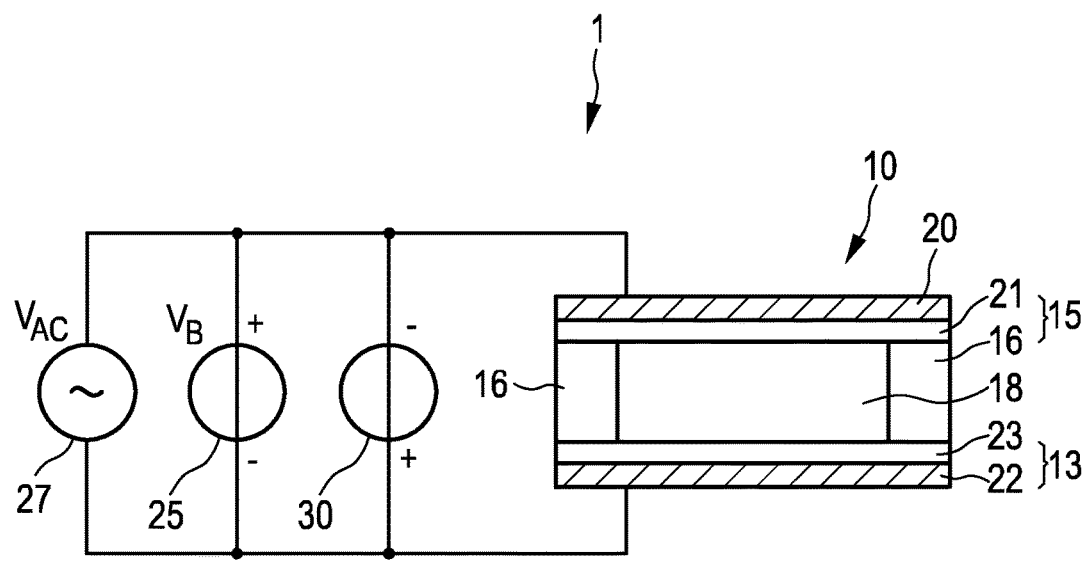
FIG. 3 shows a CMUT device according to an embodiment of the present invention.
Figure 4:
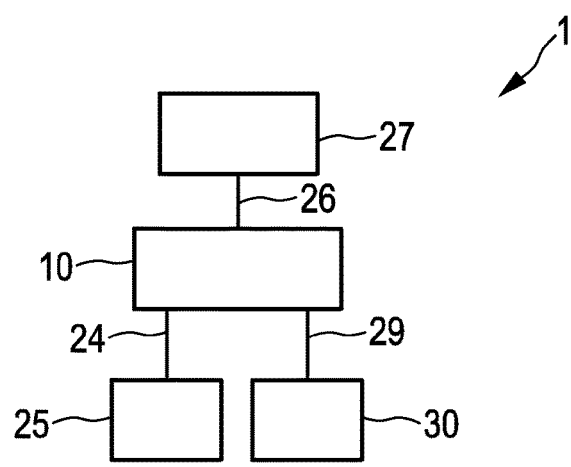
FIG. 4 shows a schematic block diagram of a CMUT device according to a first embodiment of the present invention, in particular the embodiment of FIG. 3.

A limitation of a CMUT device with such dielectric layer(s) can be that if excessive operating bias voltages are applied to the device, the dielectric layer(s) used to separate the electrodes 20, 22 can become more or less permanently charged. FIG. 3 shows a CMUT device 1 according to an embodiment. FIG. 4 shows a schematic block diagram of a CMUT device 1 according to a first embodiment, in particular the embodiment of FIG. 3. The CMUT device 1 comprises a CMUT cell 10 which comprises a substrate 13 comprising a first electrode 22, a membrane 15 comprising a second electrode 20, at least one dielectric layer 21, 22 between the first electrode 22 and the second electrode 20, and a cavity 18 formed between the substrate 13 and the membrane 15. In the example shown in FIG. 3, the CMUT cell 10 comprises a first dielectric layer 23 and a second dielectric layer 21. The substrate 13 comprises the first dielectric layer 23 and the membrane comprises the second dielectric layer 21. However, it will be understood that also just one dielectric layer could be provided, or that the electrodes 20, 22 could each be embedded in a dielectric layer.

As can be seen in FIG. 3 or FIG. 4, the CMUT device 1 comprises an alternating current (AC) source 27 for supplying an alternating current or AC signal between the first and second electrode 22, 20 for transmitting ultrasound waves. The AC source 27 is connected to the electrodes 20, 22 of the CMUT cell 10 through an AC signal terminal or connection 26. The CMUT device 1 transmits ultrasound waves (or pulses) when an alternating current or AC signal is supplied to the electrodes 20, 22 of the CMUT cell 10, and then the CMUT device 1 receives the echoes of the transmitted ultrasound waves (or pulses). For example, the alternating current source 27 can be controlled by an ASIC of the device.

The CMUT device 1 further comprises an operating bias voltage source 25 for supplying an operating bias voltage $V_B$, in particular DC voltage, of a first polarity between the first and second electrode 20, 22 during transmitting and/or receiving ultrasound waves. The operating bias voltage source 25 is connected to the electrodes 20, 22 of the CMUT cell 10 through a bias voltage terminal or connection 24. The CMUT device 1 further comprises a charging voltage source 30 for supplying an additional charging voltage $V_C$, in particular DC voltage, between the first and second electrode, the second polarity being the reverse polarity of the first polarity. The charging voltage source 30 is connected to the electrodes 20, 22 of the CMUT cell 10 through a charging voltage terminal or connection 29. By using this charging voltage source 30 the effect of trapped charges in the dielectric layer(s) can be used to increase output pressure and/or receive sensitivity of the CMUT device, in particular by supplying or applying an additional or intentional charging voltage $V_C$ between the electrodes 20, 22 having the reverse (or opposite) polarity of the polarity of the usual operating bias voltage $V_B$.

In particular, the bias voltage source 25 and the charging voltage source 30 can be implemented as separate voltage sources, as indicated in FIG. 3 and FIG. 4. This increases flexibility of the device. However, it will be understood that the operating bias voltage source and the charging voltage source could also be implemented in one single voltage source.

In a corresponding method of operating a CMUT device as described with reference to FIG. 3 and FIG. 4, the method comprises the step of supplying an operating bias voltage $V_B$ of a first polarity between the first and second electrode 20, 22 during transmitting and/or receiving ultrasound waves, in particular using the operating bias voltage source 25, and the step of supplying an additional charging voltage $V_C$ between the first and second electrode, in particular using the charging voltage source 30, the second polarity being the reverse polarity of the first polarity.

In one example or embodiment (not shown), the charging voltage is supplied during manufacturing of the CMUT device 1 such that it remains in the at least one dielectric layer 21, 23 substantially permanently (e.g. using an external voltage source which can be disconnected from the CMUT device after charging). With substantially permanently it is meant that the charge remains throughout the useful life of the device 1. In this way a substantially permanent charge is applied to the dielectric layers(s) during manufacturing and remains throughout the useful life of the device.

Figure 5:
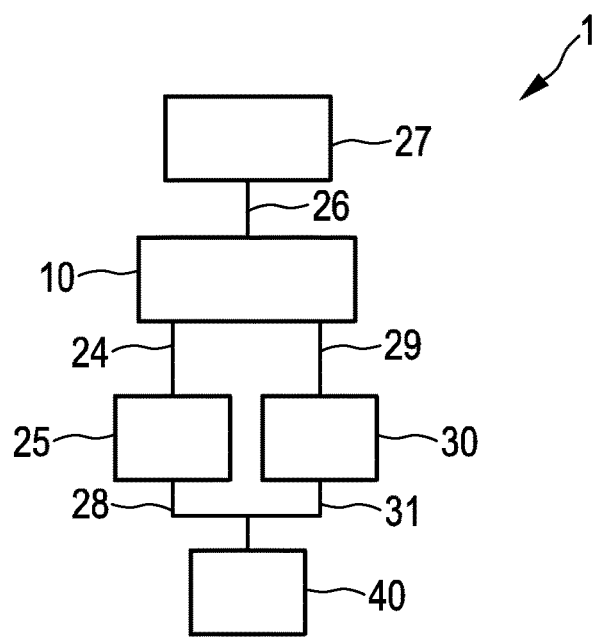
FIG. 5 shows a schematic block diagram of a CMUT device according to a second embodiment of the present invention.

Another example or embodiment will now be explained with reference to FIG. 5 which shows a schematic block diagram of a CMUT device 1 according to a second embodiment. As the second embodiment of FIG. 5 is based on the first embodiment of FIG. 4, the same explanations as to the embodiment of FIG. 4 also apply to the embodiment of FIG. 5. For example, this example or embodiment of FIG. 5 can be used if it is found that the charge cannot be permanently maintained in the dielectric layer(s). In this embodiment of FIG. 5, the CMUT device 1 further comprises a control unit 40 for controlling the operating bias voltage source 25 and/or the charging voltage 30 source to control the charge in the at least one dielectric layer 21, 23. By providing the control unit 40 in the device, the additional charging voltage $V_C$ can be supplied when actually using the device, as opposed to manufacturing the device 1. The corresponding method of operating comprises the step of controlling the operating bias voltage (or bias voltage source 25) and/or controlling the charging voltage (or charging voltage source 30) to control the charge in the at least one dielectric layer 21, 23, in particular using the control unit 40. In the embodiment of FIG. 5, the control unit 40 controls both the bias voltage source 25 and the charging voltage source 30. The control unit 40 transmits a first control signal to the bias voltage source 25 via a first control signal connection 28, and transmits a second control signal to the charging voltage source 30 via a second control signal connection 31. In particular, the first control signal is transmitted during transmitting and/or receiving of ultrasound waves, and the second control signal is not. It will be understood that also two different control units, one for the bias voltage source 25 and another one for the charging voltage source 30, can be provided. Furthermore, it will be understood that the control unit 40 can also control the AC source 27. For example, the control unit 40 can be implemented in the ASIC of the CMUT device 1.

In particular, the control unit 40 is adapted to control the operating bias voltage source 25 to supply the operating bias voltage $V_B$ for a long enough time period to provide significant accumulation of charge in the at least one dielectric layer 21, 23. In this way it is ensured that a significant charging effect is present. Furthermore, the control unit 40 is adapted to control the charging voltage source 30 to supply the charging voltage $V_C$ for a long enough time period to charge the at least one dielectric layer 21, 23 to increase output pressure and/or receive sensitivity of the CMUT cell 10. In this way the charging effect is optimally used.

Figure 7:
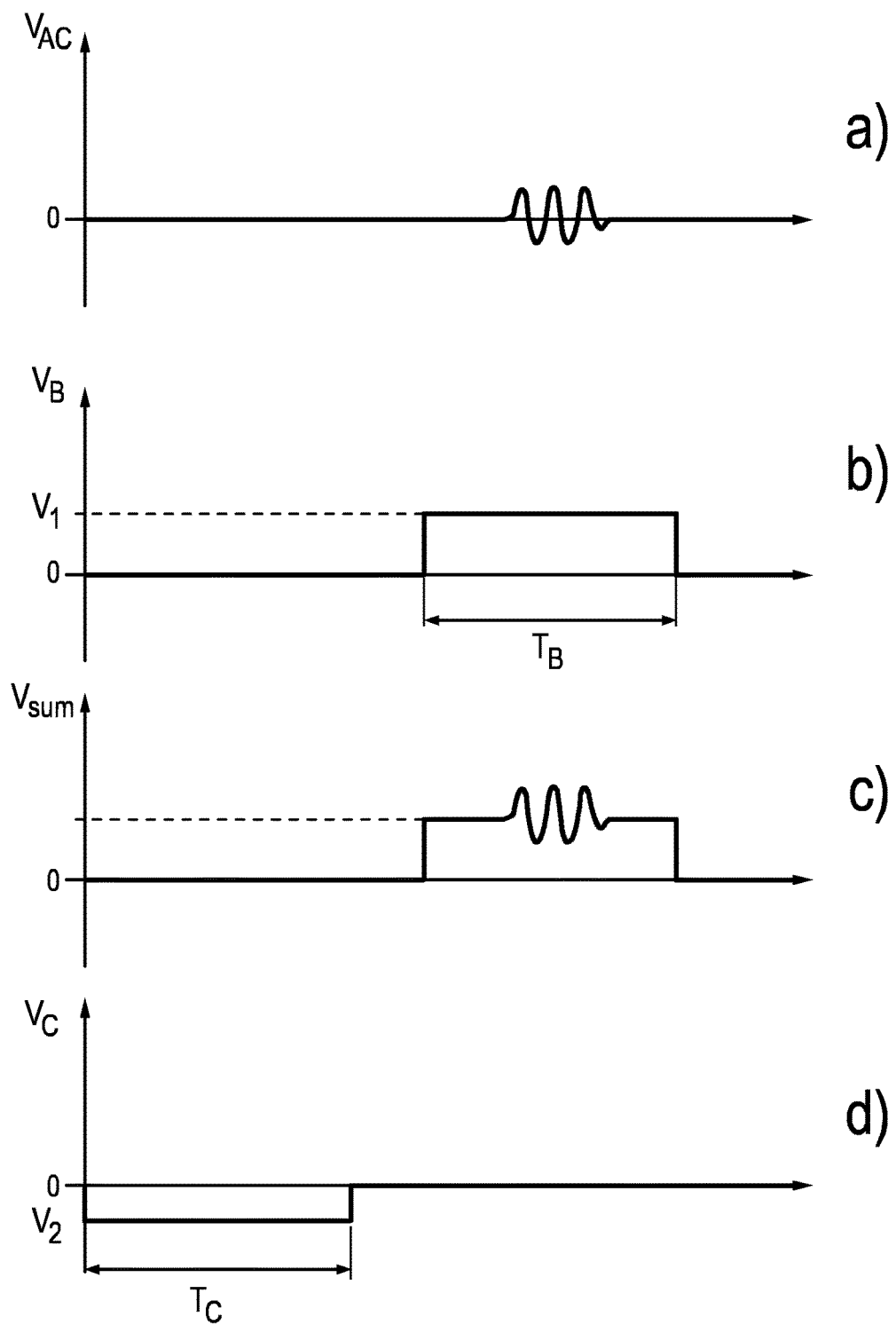
FIG. 7 shows the operation of a CMUT device according to a first example.
Figure 8:
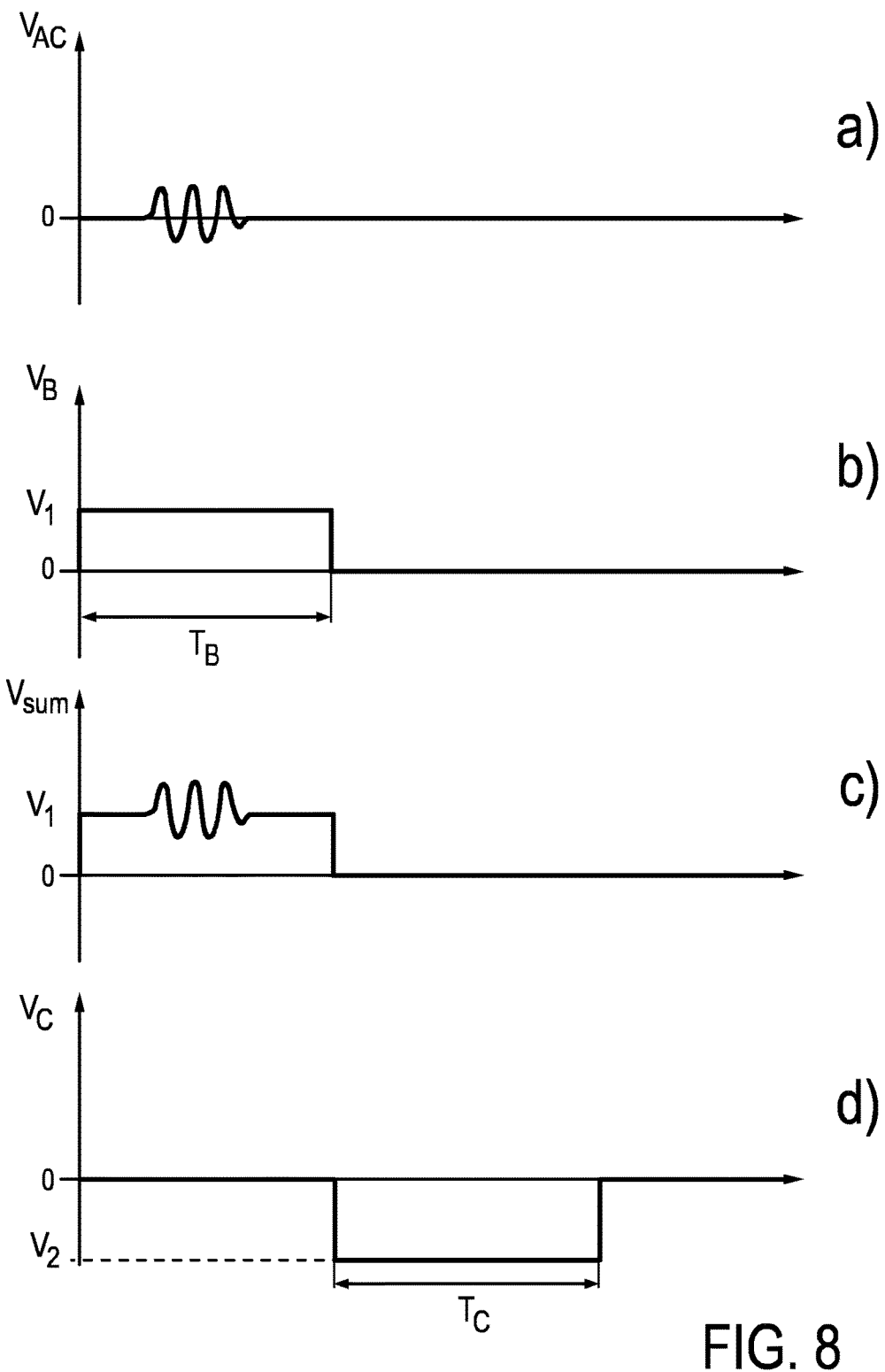
FIG. 8 shows the operation of a CMUT device according to a second example.

The operation of the CMUT device 1 will now be explained in more detail with reference to FIG. 7 and FIG. 8. FIG. 7 shows the operation of a CMUT device according to a first example, and FIG. 8 shows the operation of a CMUT device according to a second example. With reference to FIG. 7a or FIG. 8a, an alternating current or AC signal is supplied between the electrodes for transmitting ultrasound waves, for example using AC source 27 described above. As can be seen in FIG. 7b or FIG. 8b, the operating bias voltage $V_B$ is also supplied when the AC signal or voltage is supplied. Thus, the operating bias voltage $V_B$ is supplied during an operation phase of the CMUT device, i.e. during transmitting and/or receiving of ultrasound waves. For example, the operating bias voltage $V_B$ can be supplied using the operating bias voltage source 25 described above. The operating bias voltage $V_B$ is supplied for a first time $T_B$ period during transmitting and/or receiving ultrasound waves, in particular using the control unit 40 described above. The AC signal or voltage $V_{AC}$ and the bias voltage $V_B$ during the operation phase of time period $T_B$ sum up to a sum voltage $V_{sum}$, which is illustrated in FIG. 7c or FIG. 8c.

As can be seen in FIG. 7d or FIG. 8d, the additional charging voltage $V_C$ is not supplied during an operation phase, i.e. not during transmitting and/or receiving of ultrasound waves. For example, the charging voltage $V_C$ can be supplied using the charging voltage source 30 described above. The charging voltage $V_C$ is supplied for a second time period $T_C$ during no transmitting and/or receiving of ultrasound waves, in particular using the control unit 40 described above. Thus, it is ensured that the operating bias voltage $V_B$ is supplied during an operation phase of the device, and that the charging voltage $V_C$ is not supplied during such an operation phase.

In the example of FIG. 7, the second time period $T_C$ is before the first time period $T_B$. Thus, in the corresponding method of operating, first the additional charging voltage $V_C$ of the second polarity is supplied, and subsequently the operating bias voltage $V_B$ of the first, reverse polarity during the operation phase is supplied. For example, as explained above, the charging voltage can be supplied for a time period $T_C$ during manufacturing of the CMUT device such that it remains in the at least one dielectric layer 21, 23 substantially permanently, or it can be supplied when actually using the device using the control unit 40. In the example of FIG. 8, the second time period $T_C$ is after the first time period $T_B$. Thus, in the corresponding method of operating, first the operating bias voltage $V_B$ of the first polarity during the operation phase is supplied, and subsequently the additional charging voltage $V_C$ of the second, reverse polarity is supplied.

In the example of FIG. 7 or FIG. 8, the operating bias voltage $V_B$ is supplied at a first voltage level V1, and the charging voltage $V_C$ is supplied at a second voltage level V2 different from the first voltage level V1. Thus, the voltage level V2 of the charging voltage $V_C$ is not the same as the voltage level V1 of the operating bias voltage $V_B$. In the example of FIG. 7, the second voltage level V2 is smaller than the first voltage level V1. In the example of FIG. 8, the second voltage level V2 is greater than the first voltage level V1. However, it will be understood that this may also be implemented the other way round. Furthermore, it will be understood that the voltage levels could also be the same.

Even though two specific examples are illustrated in FIG. 7 and FIG. 8, it will be understood that any other suitable way of operating the CMUT device disclosed herein can be used. For example, the example of FIG. 7 and the example of FIG. 8 can be combined. In such a case, the second time period $T_C$ would be in between two first time periods $T_B$. For example, the charging voltage $V_C$ can be supplied periodically, in particular before each scan line or before each frame. In this way, the device is intentionally charged in such a way as to increase output pressure and/or receive sensitivity during subsequent operation. Alternatively, the charging voltage $V_C$ can be supplied can be supplied only once, for example during manufacturing, or only if needed, as for example determined by a monitoring unit which will be described in the following.

Figure 6:
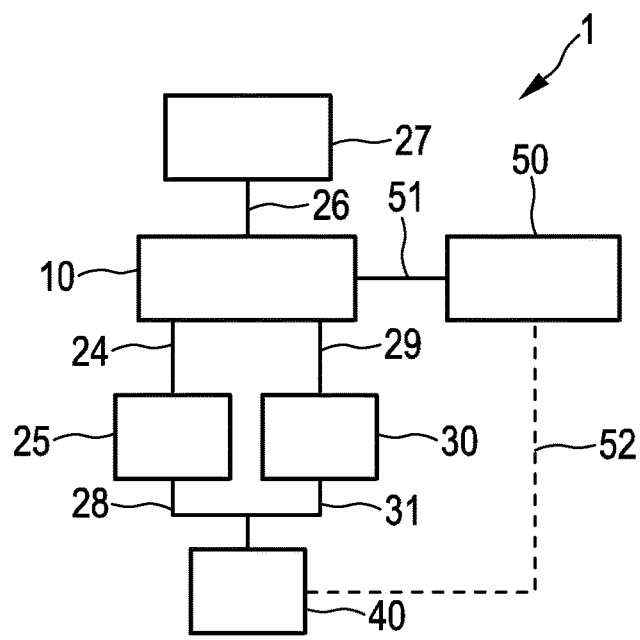
FIG. 6 shows a schematic block diagram of a CMUT device according to a third embodiment of the present invention.

FIG. 6 shows a schematic block diagram of a CMUT device according to a third embodiment. As the third embodiment of FIG. 6 is based on the second embodiment of FIG. 5, the same explanations as to the embodiment of FIG. 5 also apply to the embodiment of FIG. 6. In the embodiment of FIG. 6, the CMUT device 1 further comprises a monitoring unit 50 for monitoring the charge in the at least one dielectric layer 21, 23. In the embodiment of FIG. 6, the monitoring unit 50 is connected to the CMUT cell 10 via a connection 51. In this way it can be monitored or checked if the charge in the dielectric layer(s) 21, 23 can still increase the output pressure and/or receive sensitivity of the device. For example, the monitoring unit can be implemented in the ASIC of the CMUT device as explained above. In particular, the control unit 40 and the monitoring unit 50 can be implemented in the same device, such as the ASIC of the CMUT device In one example, the monitoring unit 50 is adapted to monitor a shift in a capacitance-versus-voltage curve of the CMUT device. In this example, the capacitance (between the electrodes 20, 22) can be measured via the connection 51 between the monitoring unit 50 and the CMUT cell 10, and the bias voltage $V_B$ can be measured via another connection (not shown in FIG. 6) between the monitoring unit 50 and the bias voltage source 25 or the control unit 40. In this way the capacitance-versus-voltage curve can be measured and then a shift can be monitored or detected therein.

In another example, the monitoring unit 50 is adapted to monitor the output pressure and/or receive sensitivity while varying the charging voltage. In this example, the output pressure and/or receive sensitivity can be measured via the connection 51, and the charging voltage $V_C$ can be varied via another connection (not shown in FIG. 6) between the monitoring unit 50 and the charging voltage source 30 or the control unit 40. In particular, a charging voltage can be determined that results in minimum acoustic pressure and/or sensitivity. For example, the operating bias voltage and the charging voltage can be monitored, while also measuring the acoustic output pressure (e.g. by using a hydrophone). When the charging voltage is applied or supplied, it can be measured that the acoustic output pressure increases.

The monitoring unit 50 can be adapted to detect when the charge in the at least one dielectric layer is insufficient, in particular by comparing the currently monitored charge with a predefined value. For example, the currently measured shift in the capacitance-versus-voltage curve can be compared with a predefined value, or the currently measured output pressure and/or receive sensitivity can be compared with a predefined value. The control unit 40 can then be adapted to control the charging voltage source 30 to reapply the charging voltage when the monitoring unit 50 detects that the charge in the at least one dielectric layer is insufficient. For example, when the monitoring unit 50 detects insufficiency of charge a corresponding signal can be transmitted via connection 52 (indicated by dashed line in FIG. 6) between the monitoring unit 50 and the control unit 40. In this way the charge in the dielectric layer(s) can be refreshed over the useful life of the CMUT device. This enables to sustain improved output pressure and/or receive sensitivity. For example, the CMUT device can be in its normal operation until a time, when the output pressure and/or receive sensitivity has decreased and the CMUT device needs to be charged again with the charging voltage to achieve the desired output pressure and/or receive sensitivity.

The CMUT device 1 described herein can be used in a variety of applications. For example, the CMUT device 1 described herein can be used in a medical ultrasound system (e.g. diagnostic or therapeutic medical ultrasound system), in particular with ultrasound imaging functionality. In particular, the CMUT device 1 described herein can be a high-intensity focused ultrasound (HIFU) transducer device. A HIFU transducer device can for example be used in a medical system to heat and destroy pathogenic tissue rapidly through ablation. A high output pressure is required in a HIFU transducer device. Therefore the charging effect can be used in an optimal way for such a HIFU transducer device.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A capacitive micro-machined ultrasound transducer (CMUT) device for transmitting and/or receiving ultrasound waves, comprising:
    at least one CMUT cell comprising:
        a substrate comprising a first electrode,
        a membrane comprising a second electrode,
        a cavity formed between the substrate and the membrane, and
        at least one dielectric layer between the first electrode and the membrane, wherein the dielectric layer is configured to hold trapped charges that increase output pressure and/or receive sensitivity of the CMUT cell, and wherein the dielectric layer extends in the cavity to prevent electrical contact between the first electrode and the membrane,
    the CMUT device further comprising:
        an operating bias voltage source for supplying an operating bias voltage ($V_B$) of a first polarity between the first and second electrode during transmitting and/or receiving ultrasound waves in a plurality of scan time periods of ultrasound imaging,
        a charging voltage source for supplying an additional charging voltage ($V_C$) of a second polarity between the first and second electrode, the second polarity being the reverse polarity of the first polarity, and
        a control unit for controlling the charging voltage source to supply the charging voltage for a long enough time period between two of the plurality of scan time periods of the ultrasound imaging to charge the at least one dielectric layer to generate the trapped charges to create a semi-permanent voltage in the at least one dielectric layer while the operating bias voltage source is disabled.

2. The CMUT device of claim 1, wherein the at least one dielectric layer includes at least some other trapped charges that are generated during manufacturing of the CMUT device that remain in the at least one dielectric layer substantially permanently during a life of the CMUT device.

3. The CMUT device of claim 1, wherein the control unit is further adapted to control the operating bias voltage source.

4. The CMUT device of claim 3, wherein the control unit is adapted to control the operating bias voltage source to supply the operating bias voltage ($V_B$) for a long enough time period to provide significant accumulation of charge in the at least one dielectric layer.

5. The CMUT device of claim 1, wherein the control unit is adapted to control the operating bias voltage source to supply the operating bias voltage ($V_B$) for a first time period ($T_B$) during transmitting and/or receiving ultrasound waves, and to control the charging voltage source to supply the charging voltage ($V_C$) for a second time period ($T_C$) during no transmitting and/or receiving of ultrasound waves.

6. The CMUT device of claim 1, wherein the control unit is adapted to control the charging voltage source to supply the charging voltage ($V_C$) periodically during gap time periods between at least some of the plurality of scan time periods, in particular before each scan line or before each frame.

7. The CMUT device of claim 3, wherein the control unit is adapted to control the operating bias voltage source to supply the operating bias voltage ($V_B$) at a first voltage level (V1), and to control the charging voltage source to supply the charging voltage ($V_C$) at a second voltage level (V2) different from the first voltage level (V1).

8. The CMUT device of claim 1, further comprising a monitoring unit for monitoring the charge in the at least one dielectric layer.

9. The CMUT device of claim 8, wherein the monitoring unit is adapted to monitor a shift in a capacitance-versus-voltage (CV) curve of the CMUT device, or to monitor the output pressure and/or receive sensitivity while varying the charging voltage ($V_C$).

10. The CMUT device of claim 8, wherein the monitoring unit is adapted to detect when the trapped charges in the at least one dielectric layer is below a predetermined value.

11. The CMUT device of claim 10, wherein the control unit is adapted to control the charging voltage source to reapply the charging voltage ($V_C$) to increase the trapped charges when the monitoring unit detects that the trapped charge in the at least one dielectric layer is below the predetermined value.

12. The CMUT device of claim 1, wherein the control unit and the monitoring unit are implemented in the same device, in particular in an ASIC of the CMUT device.

13. The CMUT device of claim 1, further comprising an alternating current source for supplying an alternating current ($V_{AC}$) between the first and second electrode for transmitting ultrasound waves.

14. The CMUT device of claim 1, wherein the CMUT device is a high-intensity focused ultrasound (HIFU) transducer device.

15. A method of operating a capacitive micro-machined ultrasound transducer (CMUT) device comprising at least one CMUT cell comprising a substrate comprising a first electrode, a membrane comprising a second electrode, a cavity formed between the substrate and the membrane, and at least one dielectric layer between the first electrode and the membrane that is configured to hold trapped charges that increase output pressure and/or receive sensitivity of the CMUT cell and to prevent electrical contact between the first electrode and the membrane, the method comprising the steps of:

supplying an operating bias voltage ($V_B$) of a first polarity between the first and second electrode during transmitting and/or receiving ultrasound waves in a plurality of scan time periods of ultrasound imaging; and supplying a charging voltage ($V_C$) of a second polarity between the first and second electrode for a long enough time period between two of the plurality of scan time periods of the ultrasound imaging to generate the trapped charges in the at least one dielectric layer to create a semi-permanent voltage in the at least one dielectric layer while the operating bias voltage is disabled, the second polarity being the reverse polarity of the first polarity.

* * * * *